(12) United States Patent
Afilani (10) Patent No.: US 6,496,114 B1
(45) Date of Patent: Dec. 17, 2002

(54) METHOD AND APPARATUS USING LASER ENHANCED DIELECTROKINESIS TO LOCATE ENTITIES

(75) Inventor: Thomas L. Afilani, Jersey Shore, PA (US)

(73) Assignee: DKL International, Inc., Wilmington, DE (US)

( * ) Notice: Subject to any disclaimer, the term of this patent is extended or adjusted under 35 U.S.C. 154(b) by 0 days.

(21) Appl. No.: 09/600,780

(22) PCT Filed: Jan. 21, 1999

(86) PCT No.: PCT/US99/01371

§ 371 (c)(1), (2), (4) Date: Sep. 21, 2000

(87) PCT Pub. No.: WO99/38135

PCT Pub. Date: Jul. 29, 1999

Related U.S. Application Data (60) Provisional application No. 60/072,146, filed on Jan. 22, 1998.

(51) Int. Cl.[7] .............................................. G08B 23/00
(52) U.S. Cl. .............................. 340/573.1; 340/568.1; 340/557; 324/452; 324/457; 324/72; 324/71.1
(58) Field of Search ........................... 340/573.1, 568.1, 340/561, 562, 565, 567, 563, 564, 566, 557; 324/452, 457, 72, 71.1

(56) References Cited

U.S. PATENT DOCUMENTS

| | | | |
|---|---|---|---|
| 4,632,762 A | | 12/1986 | Ramsland |
| 5,134,386 A | * | 7/1992 | Swanic ........................ 340/541 |
| 5,227,784 A | * | 7/1993 | Masamori et al. ........... 340/903 |
| 5,331,396 A | * | 7/1994 | Yukawa et al. .............. 350/237 |
| 5,543,018 A | * | 8/1996 | Stevens et al. .............. 204/461 |
| 5,559,496 A | * | 9/1996 | Dubats ........................ 340/539 |
| 5,748,088 A | | 5/1998 | Afilani |
| 5,870,189 A | * | 2/1999 | Uesugi et al. ............... 356/335 |
| 5,900,131 A | * | 5/1999 | Stevens et al. .............. 204/461 |
| 6,005,707 A | * | 12/1999 | Berggren et al. ........... 359/322 |
| 6,027,216 A | * | 2/2000 | Guyton et al. .............. 351/200 |

* cited by examiner

Primary Examiner—Nina Tong
(74) Attorney, Agent, or Firm—Nixon & Vanderhye P.C.

(57) ABSTRACT

A method and apparatus for locating various entities, including animate human beings and animals, as well as inanimate objects, such as, for example, certain types of plastics, observes and detects a force and subsequent resulting torque, acceleration, vibration or other measurable quantifiable manifestation of the force created by the non-uniform three-dimensional electric field spatial gradient pattern exhibited uniquely by the entity or object. Incorporation of laser energy enhances detection. Specifically, the inclusion of laser radiation enhances a dielectrokinetic effect by creating a localized region of significantly higher dielectric constant via absorption of the laser radiation by the air, and other properties which in turn significantly increases the dielectrophoretic force and resulting torque, and lowers the response time by preferentially directionally orienting or channeling the non-uniformity of the electric field line generated by the entity or object target towards the laser beam region. The laser's effect enhances the operational performance of dielectrokinetic detection devices by improving the range of detection, the strength of force and resulting torque manifestation in the locator device, and the ultimate speed of the locator device.

33 Claims, 12 Drawing Sheets

METHOD AND APPARATUS USING LASER ENHANCED DIELECTROKINESIS TO LOCATE ENTITIES

This application is a U.S. National Phase application based on PCT International Application No. PCT/US99/01371, filed Jan. 21, 1999, which claims the benefit of U.S. Provisional Application No. 60/072,146, filed Jan. 22, 1998, the contents of which are hereby incorporated by reference.

BACKGROUND OF THE INVENTION

1. Field of the Invention

The present invention relates to a method and apparatus for enhancing the detection of various entities and objects using dieletrokinesis. In particular, the instant invention is directed to a method and apparatus for locating various entities, including animate human beings and animals, as well as inanimate objects, such as for example, certain types of plastics, by observing and detecting a force and subsequent resulting torque, acceleration, vibration or other measurable quantifiable manifestation of the force created by the non-uniform three-dimensional electric field spatial gradient pattern exhibited uniquely by the entity or object and being detected by the device of the present invention as used by the device's human operator. According to the present invention, incorporation of laser energy produces a localized region by which the dielectrophoresis force and torque are significantly increased, thereby enhancing detection when compared to devices that do not use lasers.

2. Description of Related Art

The detection of animate entities and inanimate objects presence and/or absence, irrespective of the presence of intervening vision-obstructing structures, electromagentic interference (EMI), weather conditions, and the like, has uses in diverse applications, including law enforcement, military operations, firefighting and rescue, emergency services, transportation security in pre-boarding airplanes, trains and automobiles, construction (new and old), anti-shoplifting protection, and various other security and non-security related fields and operations.

My prior U.S. Pat. No. 5,748,088, entitled "Device and Method Using Dielectrokinesis to Locate Entities", issued May 5, 1998, the disclosure of which is incorporated herein by reference in its entirety, describes the use of a phenomenon known as dielelectrophoresis and resulting dielectrokinesis to detect the presence and/or absence of entites regardless of whether the entities being detected are visually obscured.

In summary, as described in detail in U.S. Pat. No. 5,748,088, dielectrophoresis describes the force and subsequent torque mechanical behavior of initially neutral matter that is dielectrical polarization charged via induction by external spatially non-uniform electric fields. The severity of the spatial non-uniformity of the electric field is measured by the spatial gradient, i.e., spatial rate of change, of the electric field. The fundamental operating principle of the dielectrophoresis effect is that the force (or torque) generated always seeks to point in the same direction, i.e., toward the maximum local electric field gradient, independent of time or sign (+/−).

The dielectrophoretic force depends upon five factors that are multiplied together to arrive at the force. These factors include: shape and volume of the initially neutral matter; the relative polarizability of the neutral matter and the surrounding media (e.g., air, air plus barriers, water vapor, etc.); the external electric field; and the spatial gradient of the external electric field. See, e.g., H. A. Pohl, Dielectrophoresis, Cambridge University Press (1978).

The device described in U.S. Pat. No. 5,748,088 uses the force resulting from the non-uniform electric field squared spatial gradient three-dimensional pattern exhibited uniquely by an entity to indicate the precise location and direction of the subject entity relative to the device's operator. The electrokinetic effect known as dieletrophoresis is used to induce a force and subsequent resulting torque on an antenna and other component parts of the device to provide a rapid directional location indication of the subject entity.

Additionally, my co-pending U.S. patent application Ser. No. 09/071,825, entitled "Inanimate Entity Line-of-Bearing Location Method Via Linking Material-Specific Non-Uniform Static Electrification Spatial Gradient Pattern to Dielectrophoresis", filed May 4, 1998, and U.S. patent application Ser. No. 09/071,806, entitled "Animate Entities Line-of-Bearing Location Device and Method Linking Species Specific Non-Uniform Electric Field Pattern of Heart ECG to Dielectrophoresis", filed May 4, 1998, the disclosures of which are incorporated herein by reference in their entireties, describe the use of dielectrophoresis to detect the location of inanimate materials and animate entities by coupling the non-uniform electric field spatial gradient pattern via dielectrophoresis to a characteristic force and subsequent torque on a high aspect ratio (length/radius) antenna and selective dielectric polarization matching and filtering components in a locating device giving a real-time updated line-of-bearing to the entity or material maximum surface electric field spatial gradient and hence to the entity or object itself, even if an entity is located behind vision-obscuring barriers made of metals, dielectrics, plastics, earth, wood, etc. and/or EMI is present.

However, the method and device of U.S. Pat. No. 5,748,088, U.S. patent application Ser. No. 09/071,825 and U.S. patent application Ser. No. 09/071,806 have certain limitations relating to ultimate range (i.e., maximum distance of detection), strength of force and subsequent torque manifestation, and the line-of-bearing locator response time. Accordingly, what is needed is a means for improving and enhancing the effectiveness of known detection devices that rely on dielectrokinesis for detecting entities and objects.

SUMMARY OF THE INVENTION

The present invention provides an improved and enhanced method and apparatus using dielectrokinesis to locate objects and entities that overcomes the limitations attendant with previous dielectrokinetic detection devices and is an improvement over my prior inventions described in U.S. Pat. No. 5,748,088 and U.S. patent application Ser. Nos. 09/071,825 and 09/071,806. In particular, the present invention uses laser energy to enhance the dielectrokinetic effect by creating a localized region of significantly higher dielectric constant via air's absorption of the laser's radiation and other properties which, in turn, significantly increases the dielectrophoretic force and resulting torque, and lowers the response time by preferentially directionally orienting or channeling the non-uniformity of the electric field line generated by the entity or object target towards the laser beam region.

Dielectrophoresis is one of five known electrokinetic effects (the other four being electrophoresis, electro-osmosis, Dorn effect, and streaming potential) and describes the forces affecting the mechanical behavior of initially neutral matter that is dielectrically polarized by induction via spatially non-uniform electric fields. The spatial non-uniformity of an electric field can be measured by the spatial gradient of the electric field. The dielectrophoresis force depends non-linearly upon several factors, including the dielectric polarizibility of the surrounding medium (air plus any intervening walls, trees, etc.), the dielectric polarizibility and geometry of the initially neutral matter (device's antenna and other component parts of the device), and the spatial gradient of the square of the target's local electric field distribution as detected at the device's antenna and other component parts. The spatial gradient is measured by the dielectrophoresis force produced by the polarization charge on the device's antenna and other component parts, and this force is a constant direction seeking force always pointing (or trying to point) the device's antenna and other component parts toward the maximum gradient in the three-dimensional non-uniform electric field squared spatial gradient pattern uniquely exhibited by a predetermined entity type.

The constant direction seeking force is highly variable in magnitude as a function of the angular position and radial position of the entity-to-be-located with respect to the device's antenna and other component parts of the device, and upon the effective dielectric polarizibilities of the intervening medium (like air) and of the materials used in the device's antenna and other component parts. The following equations define the dielectrophoresis forces wherein Equation 1 shows the force for spherical initially neutral objects (spherical antenna and the device's other component parts), and Equation 2 shows the force for cylindrical initially neutral objects (cylindrical antenna and the device's other component parts).

$$F = 2(\pi a^3)\epsilon_0 K_1 (K_2 - K_1)/(K_2 + 2K_1) \nabla |E_0|^2 \quad \text{Equation 1}$$

$$F = L/a(\pi a^3)\epsilon_0 K_1 (K_2 - K_1)/(K_2 + K_1) \nabla |E_0|^2 \quad \text{Equation 2}$$

Where:

F is the dielectrophoresis force vector detected by the antenna and the device's other component parts;

a is the radius of the sphere or cylinder;

L is the length of the cylinder (L/a is the so-called axial ratio);

$\epsilon_0$ is the permittivity constant of free space;

$K_2$ is the dielectric constant of the material in the sphere or cylinder;

$K_1$ is the dielectric constant of fluid or gas, (air) surrounding both the entity and the antenna and the device's other component parts;

$E_0$ is the electric field produced by the entity as detected by the antenna and the device's other component parts; and $\nabla$ is the spatial gradient mathematical operator.

It should be noted that the term "antenna" as used in this context includes (in a very real sense) all of the components present in the device of the present invention, including the living human operator. To this extent, the dielectric constant of the materials that make up the locator and the living human operator of the present invention all determine the overall value of $K_2$ in the above equations. These materials are not arranged in a uniform spherical or cylindrical shape, and therefore the exact value of $K_2$ and the functional relationship of $K_2$ to $K_1$ are difficult, if not impossible, to determine in a closed form of a mathematical equation. In a practical sense, experimentation has shown (and is continuing to show) the types and placement of dielectric materials needed to produce a maximum dielectrophoretic force and subsequent resulting torque, acceleration, vibration or any other measurable quantifiable manifestations of the force for precisely locating different types of entities. The following table lists some of the dielectric materials possibly used in the locator ($K_2$ values) and/or surrounding (such as air, water, walls, etc.) and the dielectric constants for these materials are:

| MATERIAL | DIELECTRIC CONSTANT |
| --- | --- |
| air | 1.0 |
| PVC | 3.0 |
| nylon | 4.0 |
| polyester | 5.5 |
| silicon | 12.0 |
| 2-propanol | 19.9 |
| water | 78.4 |
| n-maa | 191.3 |
| selenium | 1000 |
| $BaTiO_3$ | 4000 |
| $(CS_2)_n$ | 20,000 |
| metal | |
| lung | $3 \times 10^7$ |
| heart muscle | $7 \times 10^6$ |
| skeletal muscle | $1 \times 10^7$ |
| liver | $5 \times 10^7$ |
| fat (100 Hz) | $2 \times 10^5$ |
| kidney (10 kHz) | $5 \times 10^4$ |
| blood (10 kHz) | $3 \times 10^3$ |
| brain (100 kHz) | $4 \times 10^3$ |
| bone (100 Hz) | $4 \times 10^3$ |

These operating principles involve using the above-mentioned forces to point an antenna toward the maximum spatial gradient of the local electric field, to thereby indicate the direction toward an unseen entity.

According to the present invention, the performance of devices such as those described in U.S. Pat. No. 5,748,088 and U.S. patent application Ser. Nos. 09/071,825 and 09/071,806 is significantly improved and enhanced by the inclusion of laser energy directed parallel to the longitudinal axis of the antenna of the device. In particular, it has been found that inclusion of laser energy transmitted in a direction parallel to the longitudinal axis of the antenna provides significant improvement in the ultimate range (i.e., maximum range of detection), strength of force and subsequent torque manifestation, and the ultimate speed of the locator response.

As is well known, a laser is a device that generates coherent, nearly single wavelength (and frequency), highly directional electromagnetic radiation emitted in the range from submillimeter through ultraviolet and x-ray wavelengths. Light beams produced by lasers are highly coherent and monochromatic. Strong spatial coherence extends over the beam cross section, and the coherence length along the direction of propagation may be from millimeters to many meters long. In addition to measuring coherence between light at two points separated transversely (cross section) to the direction of the laser beam's propagation, measurements can also be made of mutual coherence between light at points separated along the direction of propagation. This allows one to define a coherence length $L_c$ such that strong coherence is measured when the separation between the two sampling points is less than $L_c$. A related coherence time can be defined as $t_c = L_c/c$. Measurement of $L_c$ or $t_c$ yields information on the frequency spread of the wave $\Delta f$, wherein $\Delta f \approx 1/t_c$.

Figure 6:
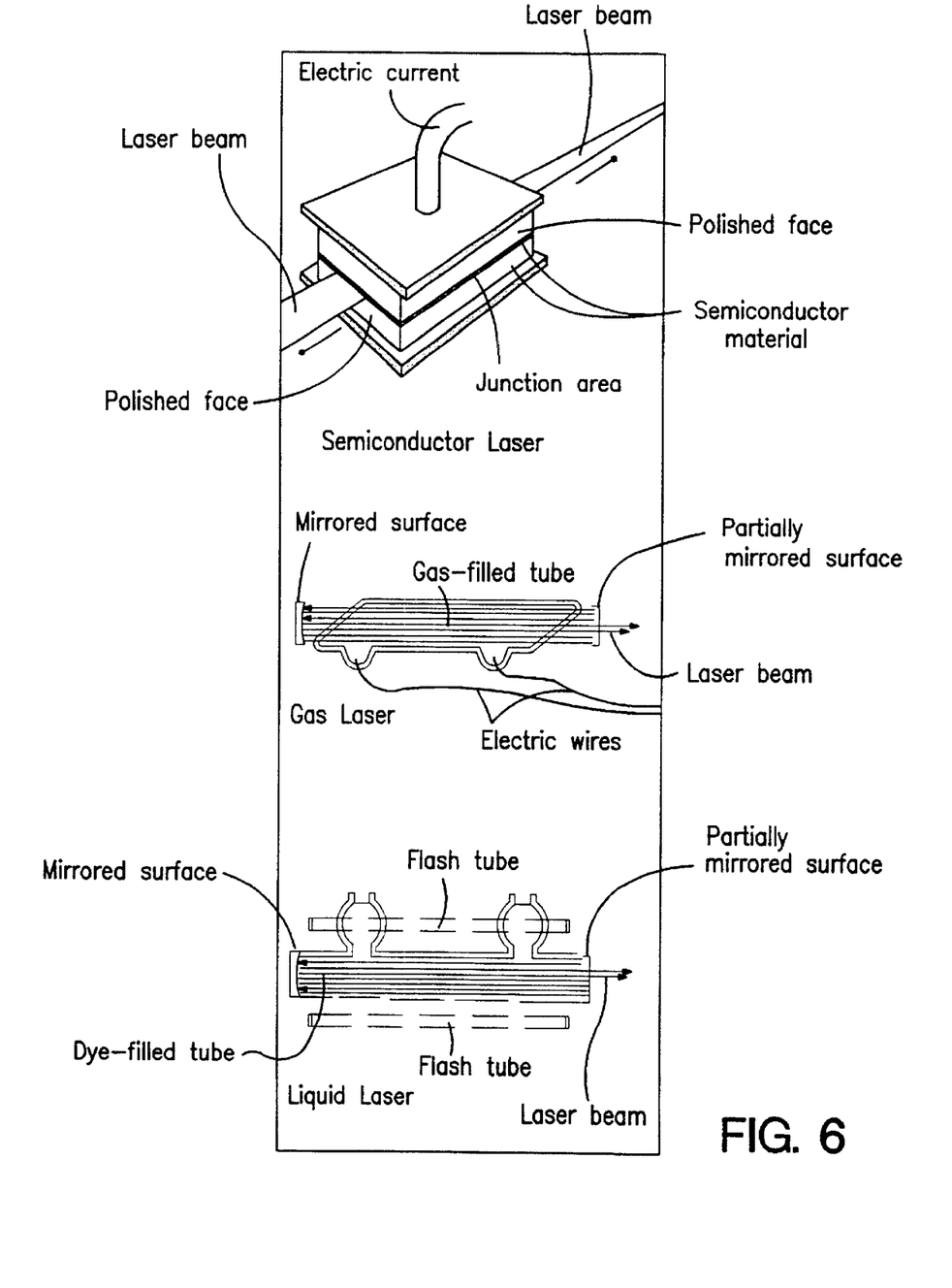
FIG. 6 are illustrative drawings of exemplary types of lasers.

There are three major types of lasers that are classified based on their light-amplifying substance: (1) solid lasers;

(2) gas lasers; and (3) liquid lasers. Examples of solid lasers include semiconductor lasers, crystal lasers, glass lasers. Semiconductor lasers, also called injection lasers, have a small cube of a semiconductor as their light-amplifying substance. A common material used is gallium arsenide. The semiconductor includes two layers that differ in their electric charge. Current passing through the semiconductor produces a continuous beam of coherent light along the junction between the two layers. Semiconductor lasers (also known as laser diodes) convert electricity into coherent light very efficiently. The small size of semiconductor lasers makes them very useful. Schematic drawings of semiconductor, liquid and gas lasers are shown, for reference, in FIG. 6.

According to the present invention, orienting a laser light beam or beams parallel to the longitudinal axis of the locator device antenna, has significantly improved the ultimate range, strength of force and resulting torque manifestation and ultimate speed of the locator response of known locator devices that rely on the dielectrokinesis phenomenon.

The laser enhances the performance of the dielectrokinetic locator devices because the laser light is partially absorbed by the air and usually nearly completely by barrier materials. This partial absorption by air produces electronic and/or thermal excitation absorption. The excitation, thus produced, provides a localized (to the region where the laser beam exists) region of significantly higher dielectric constant and other properties which, in turn, significantly increases the dielectrophoresis force and torque, while concurrently lowering the response time by preferentially directionally orienting or converging the non-uniformity of the electric field line generated by the entity or object target, towards the laser light beam region. The laser beam is characterized by its wavelength, power, coherence length and beam shape (e.g., Gaussian, focused Gaussian, etc.) all of which affect the level of enhancement observed for the dielectrokinesis force and torque provided by the invention.

In addition, it has been observed that the level of laser enhancement of the dielectrokinesis force and torque depends upon the number of lasers (i.e., larger effective volume of partially absorbed beams) and the specific geometrical arrangement of the lasers (i.e., increased convergence of electric field spatial gradient). As will be described in detail herein, multiple lasers are simultaneously operating while they are also directly attached to the entity detection device itself. For a given number of lasers, the optimum geometrical arrangement for maximum laser enhancement is the arrangement with the highest symmetry (e.g., a line for two lasers, a triangle for three lasers, a square for four lasers, etc.).

In accordance with the invention, an operator holds the locator device in hand, and through a handle, the locator device is electrically connected to the operator. The operator is partially electrically grounded (through the operator's feet), and thereby the individual human operator body's capacitance (C) and resistance (R) to true ground are connected electrically to the handle of the locator device. Ranges for individual human body's C have been measured as 100 pF to 400 pF and for individual human body's R have been measured as 0.03 K$\Omega$ to 1 M$\Omega$. Thus, the generalized electrical parameter (the polarization charge pattern induced on the device by the electric field spatial gradient of the entity in this case, but also electric field, current and voltage) exponential decay time (=RC) constant range for the variety of human being bodies potentially acting as locator device operators is about 3 to 400 $\mu$ seconds. This decay time constant is greatly increased through an externally connected series resistor of up to 100 K$\Omega$ and parallel capacitor up to 0.01 mF, which results in an effective human operator's exponential decay time constant up to 1 to 10 seconds.

This enables dielectrophoretic forces caused by the induced polarization charge pattern on the locator device antenna and other component parts to be detected, replenished instantly and locked onto since the force is replenished faster than the induced polarization charge pattern on the device can decay away to true ground through the operator's body. This effect is called, and is using, the spatially self-correcting nature of the dielectrophoretic force (always pointing or trying to point to the maximum of an entity's electric field three-dimensional squared spatial gradient pattern, which in the case of inanimate entities, may be static electrification induced).

The locator device is held in a balanced, few degrees down tilt from the exactly horizontal state, and the operator scans the locator device in a constant speed uniform linear motion back and forth. An antenna extends from the front of the locator device and is acted on along with the device's other components by the aforementioned forces. These forces create a subsequent resulting torque around a well defined pivot line which tends to make the locator device's antenna and the device's other component parts point toward the maximum spatial gradient of the square of the non-uniform electric field uniquely exhibited by any target entity within the range of the locator device.

Four internal N-channel J-FETs (field effect transistors) are connected to the locator device's antenna and operate in their non-linear range to effectively change the antenna's length. Three of these FETs are arranged in modules that are equidistant from the antenna's longitudinal axis and are spaced 120° apart. The fourth FET is arranged in a module below the axis and to the rear of the locator device. Three potentiometers are provided on the first three modules to adjust the current levels through the first three FETs and thereby tune the locator. The gain and frequency response of the fourth FET is adjusted by a six position switch connected to the base of an NPN transistor. By changing the frequency response of the locator device, the device is tuned to reject the higher frequency electromagnetic signals and noise from all external sources, including those sources associated with the human operator himself in order for the locator device to interact with and respond to only the three-dimensional non-uniform electric field squared spatial gradient pattern exhibited uniquely by a predetermined entity type.

While scanning the locator device in a constant speed uniform linear motion back and forth in front of a known or reference entity, the operator changes the six position switch until a maximum force and subsequent resulting torque is detected and used to aim the antenna and the device's other component parts toward the target entity. After selecting the setting of the six position switch, the operator adjusts the gain of the first three FETs until the locator device points or tries to point directly at the target entity. For different entities, different dielectric materials are used for the antenna and other component parts. Examples of detectable entities include metals, plastics, polymers and other inanimate materials. Continued research on the instrument has yielded positive results in the instrument's ability to be tailored both as a geometrical design and with respect to materials of construction to specifically detect a variety of different target entities.

The operation of the locator device described above is enhanced by positioning one or more laser emitting devices such that the beam or beams are emitted in a direction parallel to the longitudinal axis of the locator device antenna. In cases where more than one laser is used, it is preferably to optimize their affect on the dielectrokinetic force by arranging the beams in an optimal geometrical configuration, such as, for example, where three lasers are used the beams are arranged in a triangular configuration, i.e., the lasers are arranged to be at the points of an equilateral triangle emitting their beams transversely of plane of the triangle.

Accordingly, it is an object of this invention to enhance the dielectrokinetic effect by creating a localized region of significantly higher dielectric constant and other properties which in turn significantly increases the dielectrophoretic force and resulting torque, and lowers the response time by preferentially directionally orienting or channeling the non-uniformity of the electric field line generated by the entity or object target towards the laser beam region.

It is another object of the invention to improve the performance of previous dielectrokinetic detection and locator devices by using lasers to enhance the resulting dielectrokinetic effect of the devices.

These and other objects, and their attendant advantages, are achieved by the present invention, which provides an improved and enhanced dielectrokinetic locator device, comprising: a housing formed of a first dielectric material and having an interior with a second dielectric material therein; an auxiliary device utilizing laser emitted light oriented in a direction parallel to a longitudinal axis of the device; and a sinuous rod forming a handle, the rod having a first end extending from the interior of the housing and out a rear end of the housing, wherein an operator of the device grasps the housing and the handle and holds the device within range of an entity or object to be detected, such that the device reacts to a unique non-uniform electric field squared spatial gradient three-dimensional pattern exhibited by the entity or object to produce a dielectrophoretic force and a quantifiable manifestation of the force on the device that indicates specific direction relative to the object or entity.

BRIEF DESCRIPTION OF THE DRAWINGS

The invention will be described in detail herein with reference to the following drawings, in which like reference numerals refer to like elements, and wherein.

DETAILED DESCRIPTION OF EXEMPLARY EMBODIMENTS

Figure 1A:
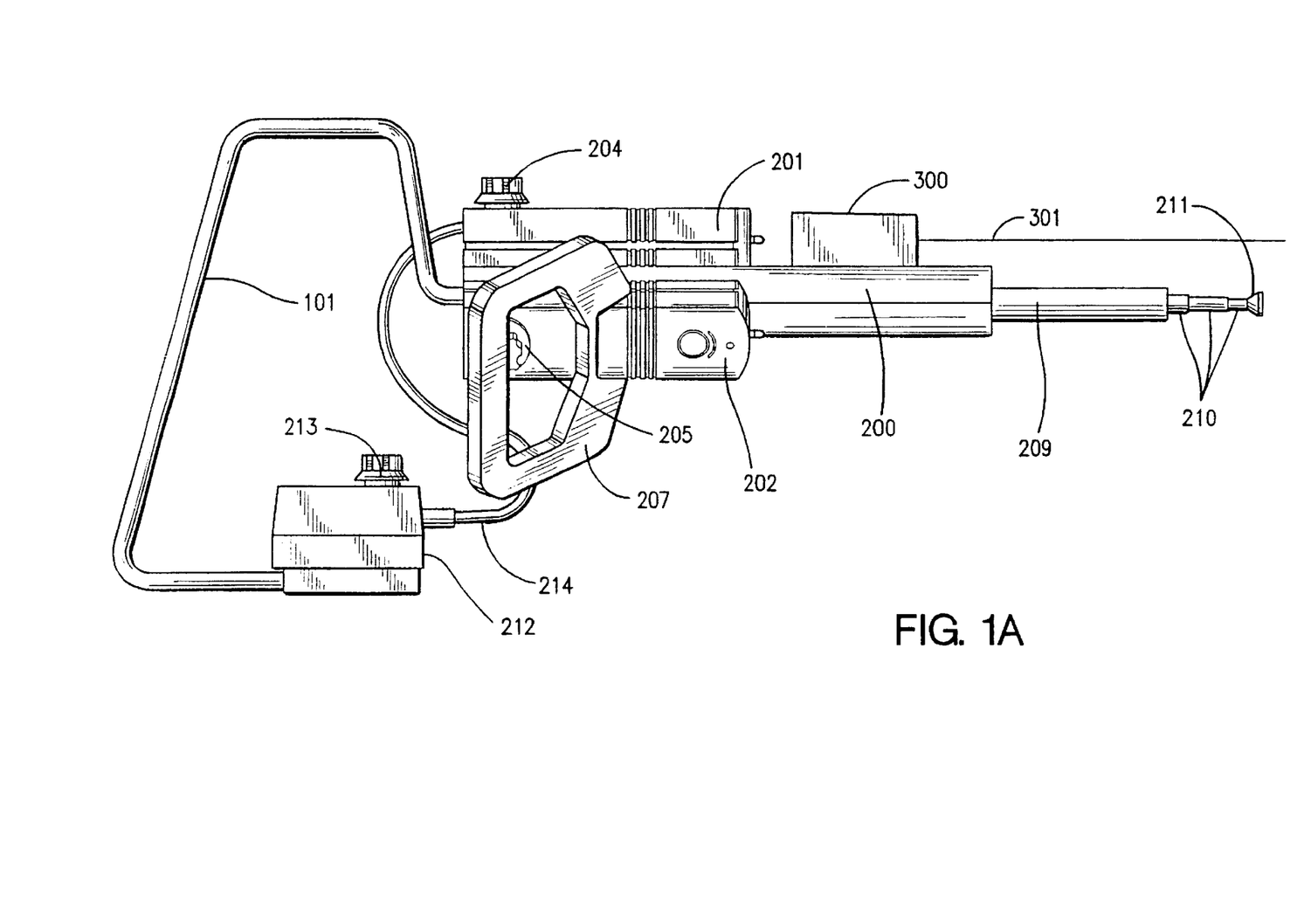
FIGS. 1A–1C are schematic drawings of a line-of-bearing locator device including an auxiliary laser device and illustratively showing the laser beam emitted therefrom.
Figure 1B:
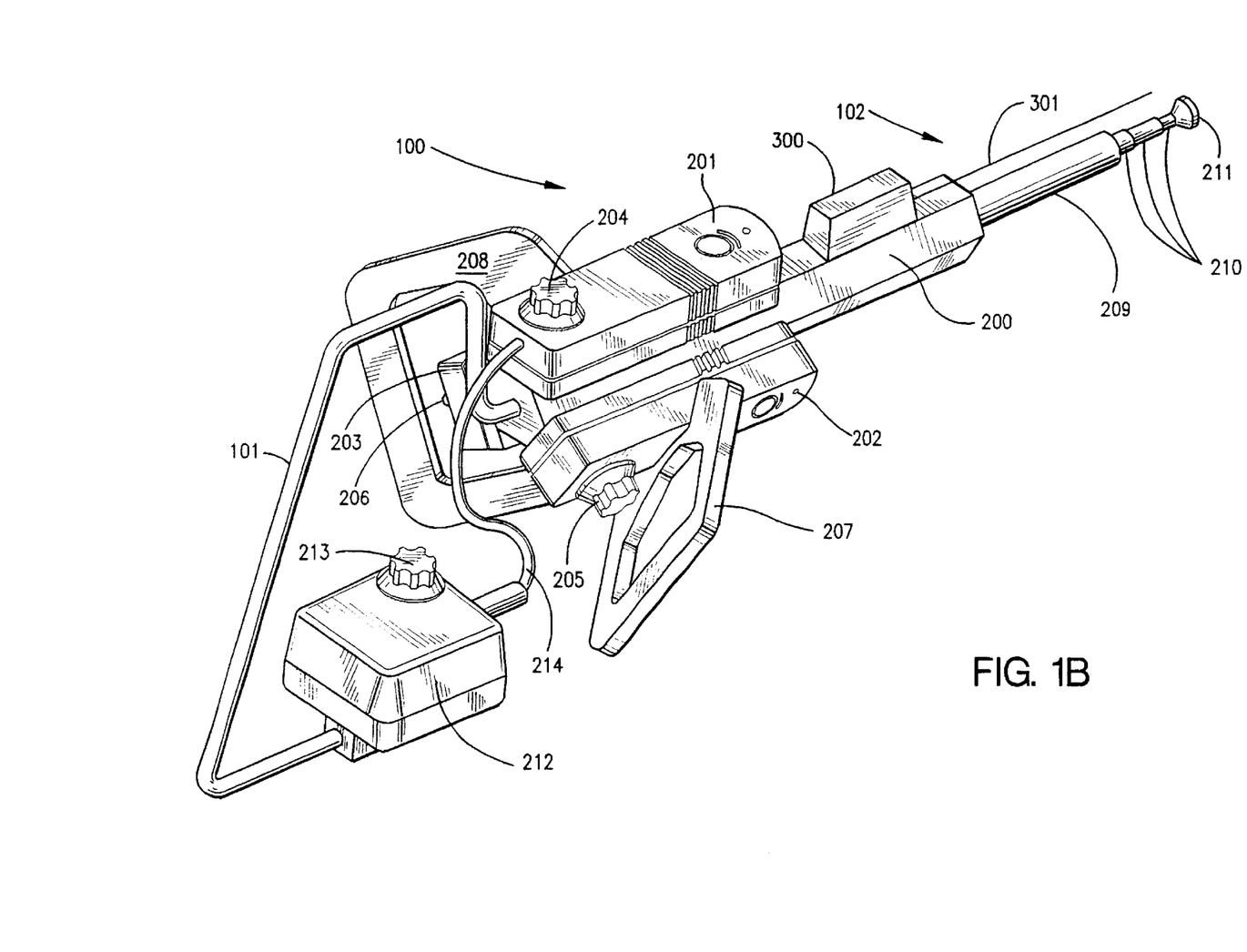
Figure 1C:
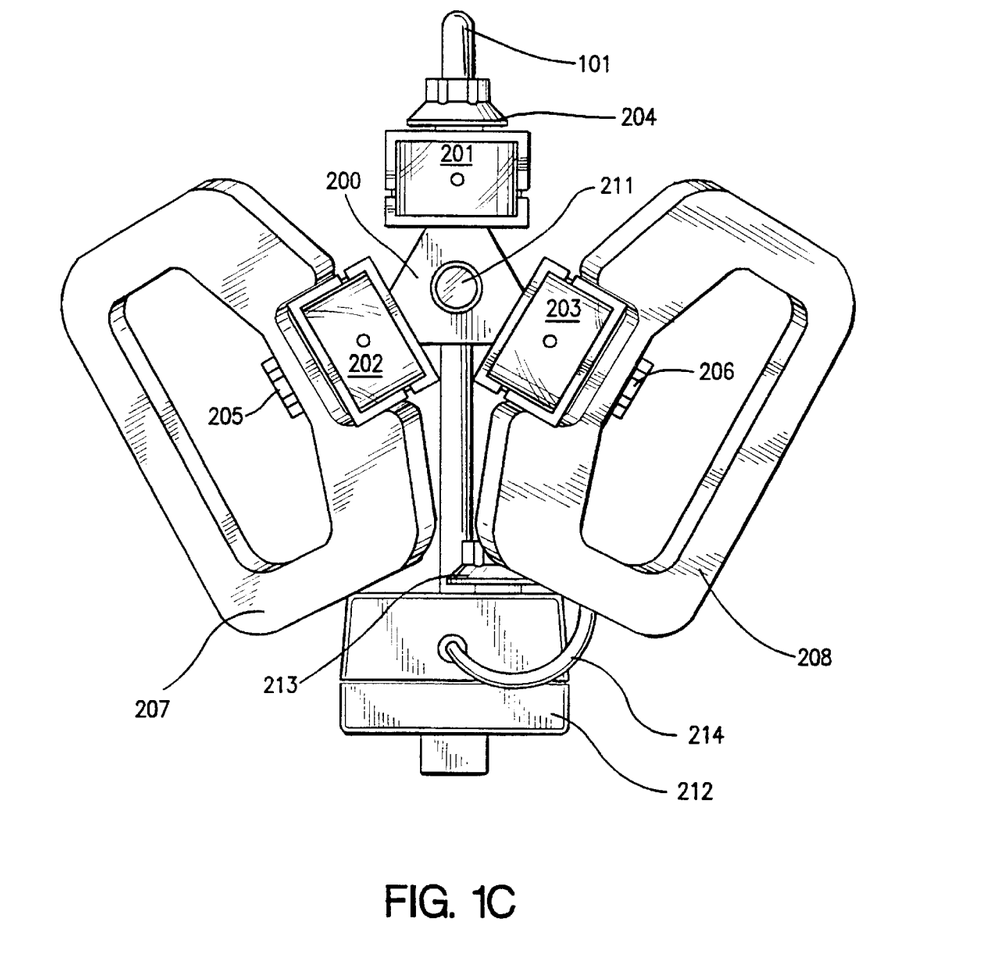
Figure 2:
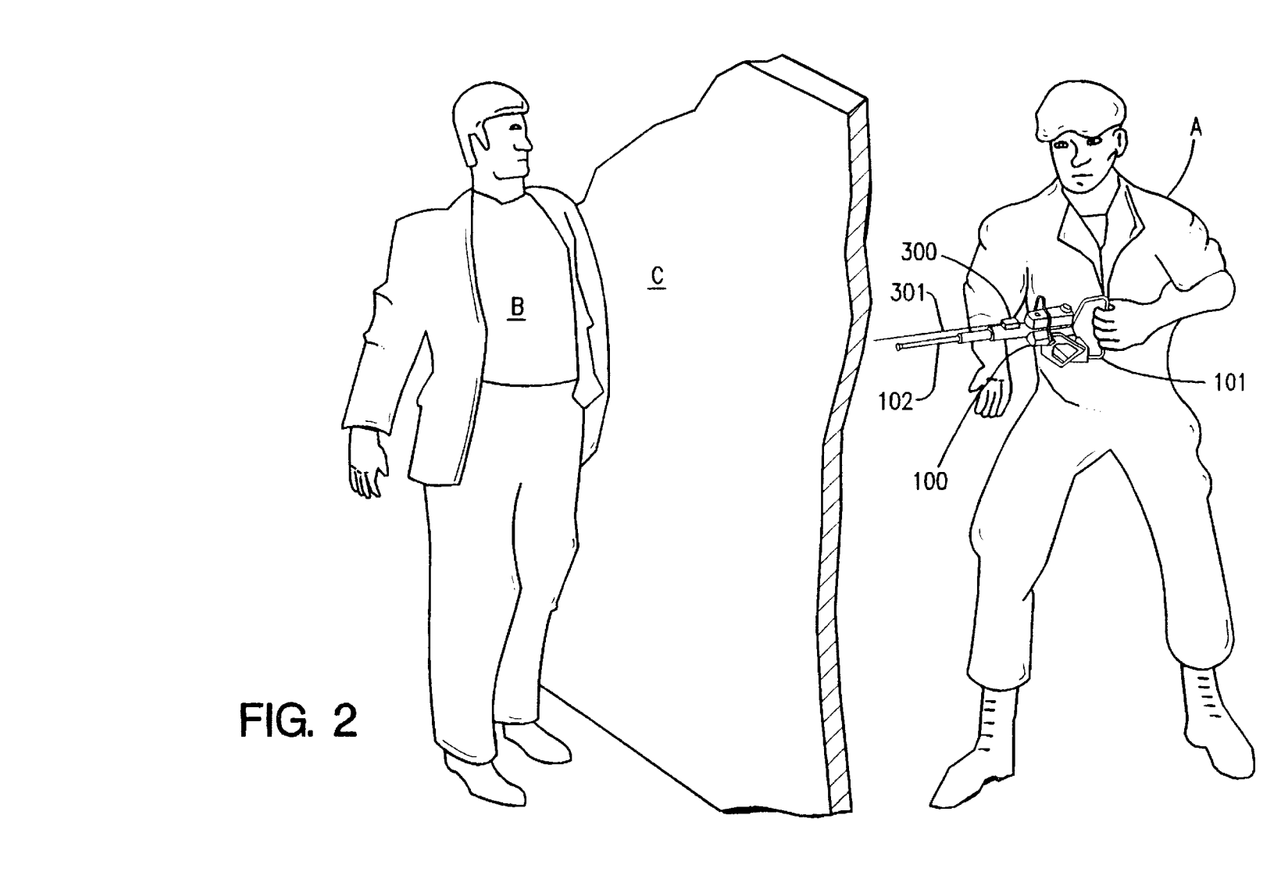
FIG. 2 is a schematic drawing of a human operator utilizing the device of the invention to detect a line-of-bearing to a human target with the presence or absence of a barrier.

Exemplary embodiments of the invention will be described in detail herein with reference to the drawings. Turning now to FIGS. 1A–1C, a schematic drawing of a line-of-bearing locator device including an auxiliary laser device and illustratively showing the laser beam emitted therefrom is shown. The antenna 102 includes a rear portion 209 made of nylon or similar material, telescoping sections 210 and an end knob 211. The antenna 102 protrudes from a central dielectric housing 200 in a preferably coaxial arrangement. It is important to note that antenna 102 does not necessarily have to be of the telescoping type, and may be a one piece rigid or flexible type antenna. Furthermore, as all of the components of the locator device 100 effectively act as an antenna, the locating device operates as described without the antenna 102 installed, although the forces produced are greatly reduced.

Attached to the central dielectric housing 200 are modules 201, 202, 203 and 300. The top module 201 is mounted directly over the common axis of the antenna 102 and the central dielectric housing 200, and in line with this axis. The lower right module 202 and the lower left module 203 are preferably spaced 120° apart from each other and the top module 201, and are also in line with the common axis. Each module 201, 202, 203 has a variable resistor control knob 204, 205, 206 associated respectively therewith. The lower left and lower right modules 203, 202 also include parabolic antennas 208, 207, respectively, both of the parabolic antennas being attached to their respective modules in a swept-back position. The handle 101 is preferably formed from a metal rod that protrudes coaxially from the central dielectric housing 200. The handle 101 bends upward, extends horizontally for a short distance and bends downward to form a handle. The handle also bends forward to provide support for a bottom tuning module 212. The tuning module 212 includes a variable resistor control knob 213 and a cable 214 that attaches to the top module 201. A laser beam emitting device 300 is disposed on top of the dielectric housing 200 such that a beam 301 emitted therefrom is parallel to the central axis. It will be understood that multiple lasers 300 may be included with the locator device 100. It is preferable that when multiple lasers are used, that the beams emitted therefrom be arranged in an optimal geometrical arrangement. For example, when three lasers are used, the beams are preferably emanating from three points of an equilateral triangle, when four lasers are used, the beams are preferably emanating from the four corners of a square, and so on.

Figure 9:
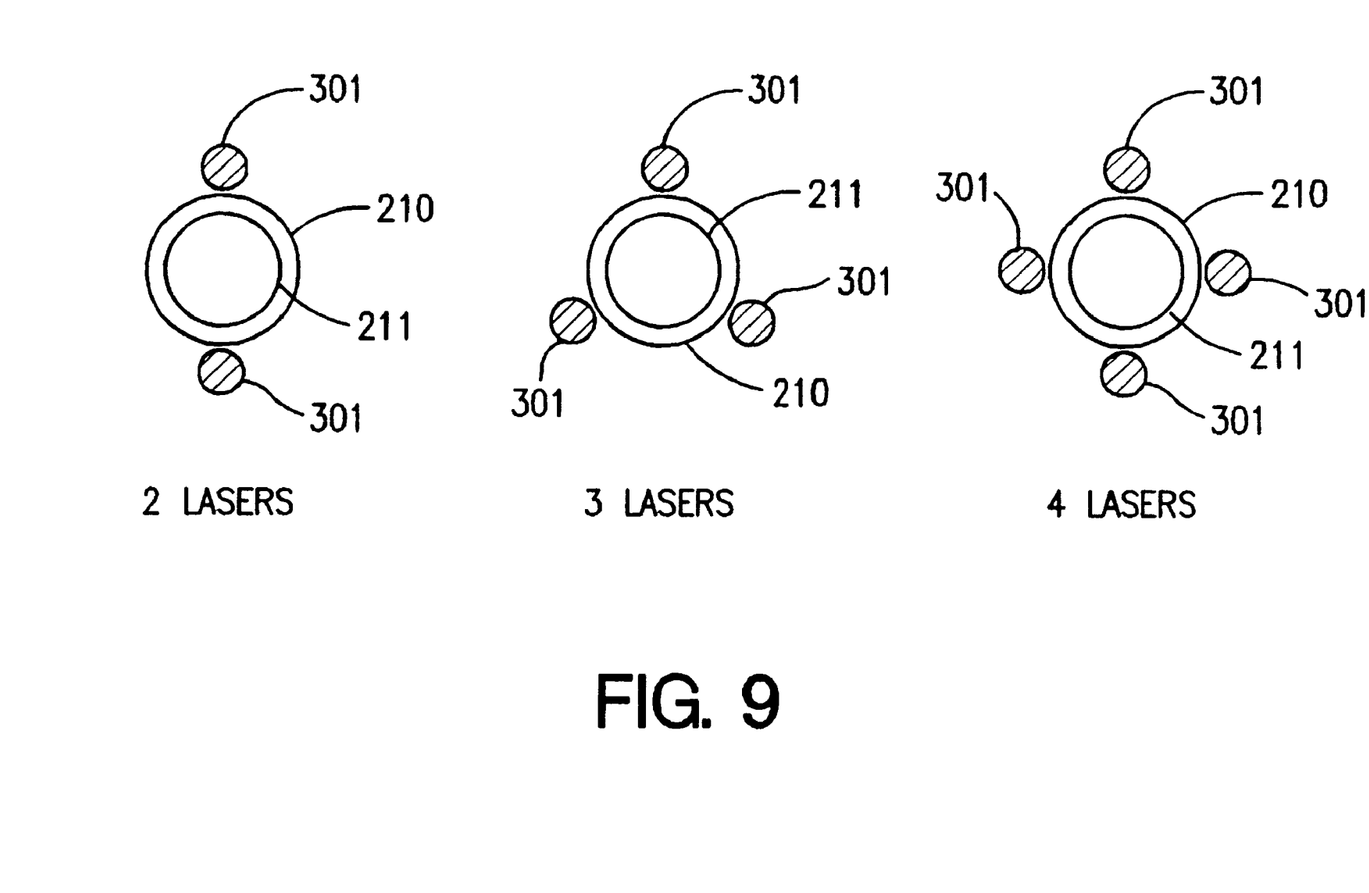
FIG. 9 illustrates multiple cross-sectional views of a front portion of the locator device according to preferred embodiments of the present invention showing optimal geometrical locations of multiple lasers.

Several transverse cross-sectional views of a front portion of the locator device 100 are shown in FIG. 9. The cross-hatched circles indicate a cross-section of the laser beam relative to the locator device 100. As shown in FIG. 9, when two lasers are used, a linear arrangement (i.e., 180° separation) is optimal, while when three lasers are used, the optimal arrangement is to position the three lasers at the corners of an equilateral triangle. When four or five lasers (not shown) are used, the lasers are optimally positioned at the corners of a square or pentagon, respectively. As shown in FIGS. 1A–1C, when one laser is used, its beam need only be parallel to the antenna.

Figure 3:
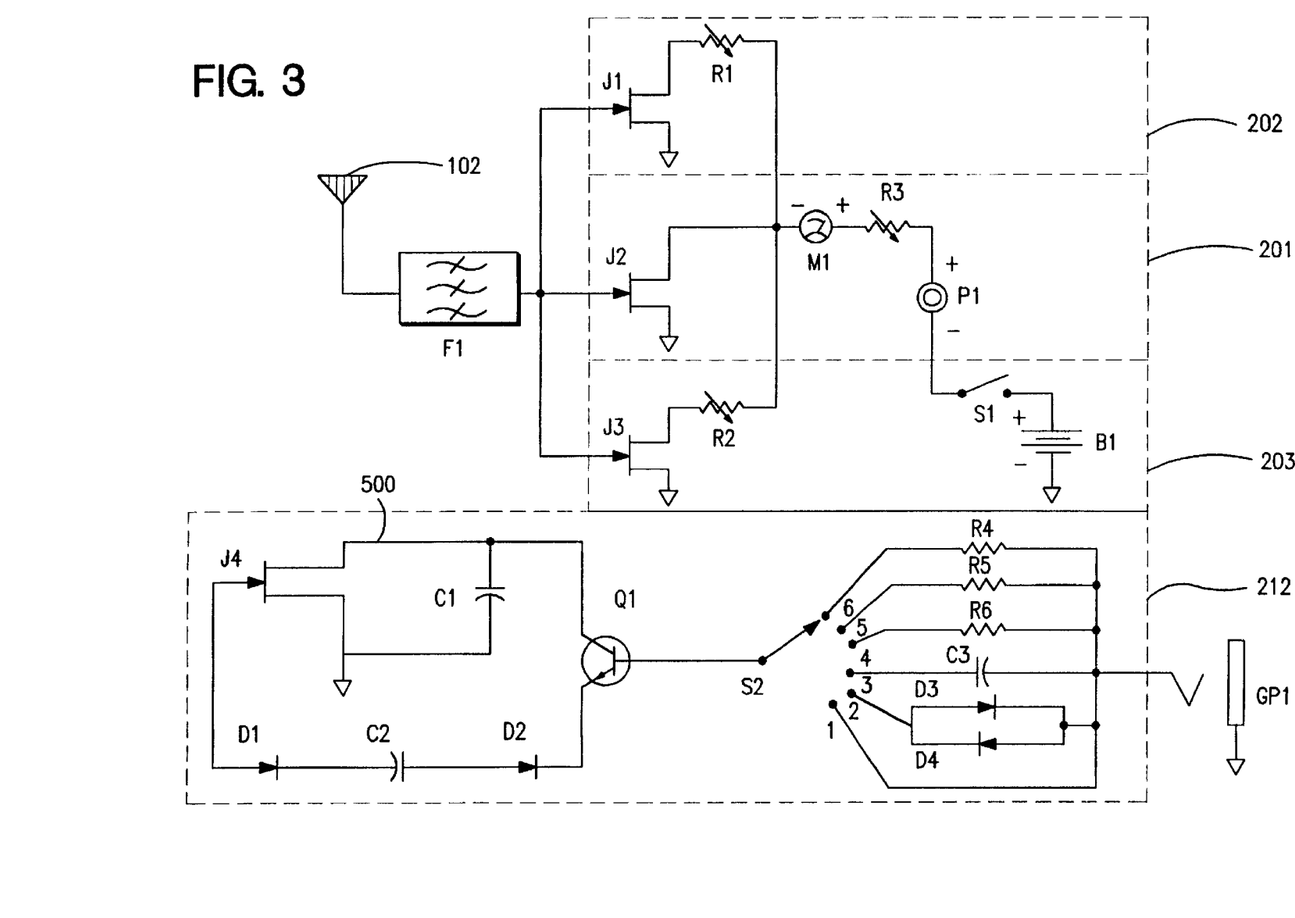
FIG. 3 is a schematic electrical circuit diagram of the three main modules and the bottom tuning module of the locating device.

The electronic circuitry for the locator device 100 is shown in FIG. 3. The antenna 102 is connected to an optimal low pass filter F1, which removes all high frequency signals and noise from all external electromagnetic sources, including those from the human operator A himself. The details of the electronic circuitry and the geometrical design and materials of construction used in the locator device 100 are chosen so as to tailor the locator device 100 for a predetermined entity type. The output from the optimal low-pass filter F1 is fed to the gate of the three N-channel field effect transistors, (FETs). The three FETs act as amplifiers and are housed one each in the three modules. The lower right module 202 contains FET J1 and a 0–100 kΩ variable resistor R1, the top module 201 contains FET J2, a DC ammeter M1, a 0–100 kΩ variable resistor R3, and a piezo buzzer P1, and the lower left module 203 contains FET J3, a 0–100 kΩ variable resistor R2, an on/off switch S1 and a 9-volt battery B1.

Variable resistors R1 and R2 adjust the current gain of FETs J1 and J3, respectively. By adjusting the gain of these FETs, the effective electrostatic effect on these devices is balanced relative to FET J2. The overall gain of FETs J1, J2 and J3, is adjusted by 0–100 kΩ variable resistor R3. The DC ammeter M1 is provided to indicate the combined current flow through all three FETs. In addition, the piezo buzzer P1 provides an audio output whose frequency increases as the current through the circuit increases. The battery B1 provides the required supply voltage (preferably nine volts) to operate the circuit, and the switch S1 provides a means for turning the amplifiers J1–J3 on and off.

The bottom module 212 contains the necessary circuitry for increasing the human operator's electrical parameter decay (RC) time constant, from $\mu$ seconds as occurs naturally to seconds as explained previously, needed to capture and lock onto the dielectrophoretic force exhibited by a target entity and the subsequent resulting torque, acceleration, vibration or any other measurable, quantifiable manifestation of the force detected by the locator device 100. A ⅛ inch grounding jack GP1 is used to provide a ground to the circuit by inserting a mating shorting plug into the jack GP1. Once inserted, the mating plug (via the jack GP1) provides a ground potential via the reference entity RE to each of 3.3 kΩ resistor R4, 22 kΩ resistor R5, 100 kΩ resistor R6, 0.01 mF capacitor C3, clipping diodes D3 and D4, and position one of a six-position selector switch S2. The six-position selector switch S2 can be moved to one of six positions to connect the base of an NPN transistor Q1 to one of the above components. The NPN transistor Q1 makes up part of a tunable circuit that also includes an N-channel FET J4, a first 0.01 $\mu$F capacitor C1, a first diode D1, a second diode D2, an electrical line 500, and a second 0.01 $\mu$F capacitor C2. By inserting or removing the shorting plug into the jack GP1 and changing the position of the switch S2, the gain of the transistor Q1 can be adjusted, and the overall frequency response of the tuned circuit in the bottom module 212 can be changed for maximum response. The extraordinarily high ULF dielectric constants for living tissues, given in the previous table, allows the human operator's electrically grounded body to directionally distort, concentrate or focus the non-uniform electric field pattern emanating from the entity target. This action greatly increases the electric field flux density near the locator device. This field line concentrating increases the torque-producing dielectrophoresis force and results in an effective increase in the amplification or gain of the locator device as the human operator samples the electric flux density as the device is moved in a uniform constant speed linear motion back and forth to initiate torque and lock-on.

The torque-produced pivoting response can be further increased by adding additional circuit elements such as capacitors, resistors and/or inductors to the circuit already described with reference to FIG. 3. These circuit elements decrease the response time of the locator device. Preferred value ranges for the elements are up to 56 mF for the capacitors, up to 5,000 MΩ for the resistors and up to 200 mH for the inductors. These circuit elements serve to modify and optimize the device's polarization response and decay time constants.

As stated earlier, all of the components in FIG. 3 act as antenna extensions that increase the dielectrophoretic force and the subsequent resulting torque that is detected by the locator device 100. Every human being, as a locator device operator, has a different capacitance (C) and resistance (R) resulting in a low exponential decay time constant (=RC) for capturing and locking onto the dielectrophoretic force and the subsequent resulting torque. By adjusting R1–R3 and S2, the individual human operator and the locator device 100 can be jointly tuned and optimized to detect the maximum dielectrophoretic force and subsequent resulting torque for the specific human being operating the locator device 100. This is accomplished by using a reference entity (such as a visible entity) and adjusting S2 and R3 until the maximum dielectrophoretic force and subsequent resulting torque are detected by the individual human operator. Once the position of S2 has been determined, the operator notes the direction the antenna is pulled relative to the reference entity. If this direction is not exactly toward the reference, R1 and R2 are adjusted until the torque on the locator device 100 tends to point the antenna 102 directly toward the reference entity. After the locator device 100 is tuned and optimized, unobserved entities can be easily located by the device.

Figure 4:
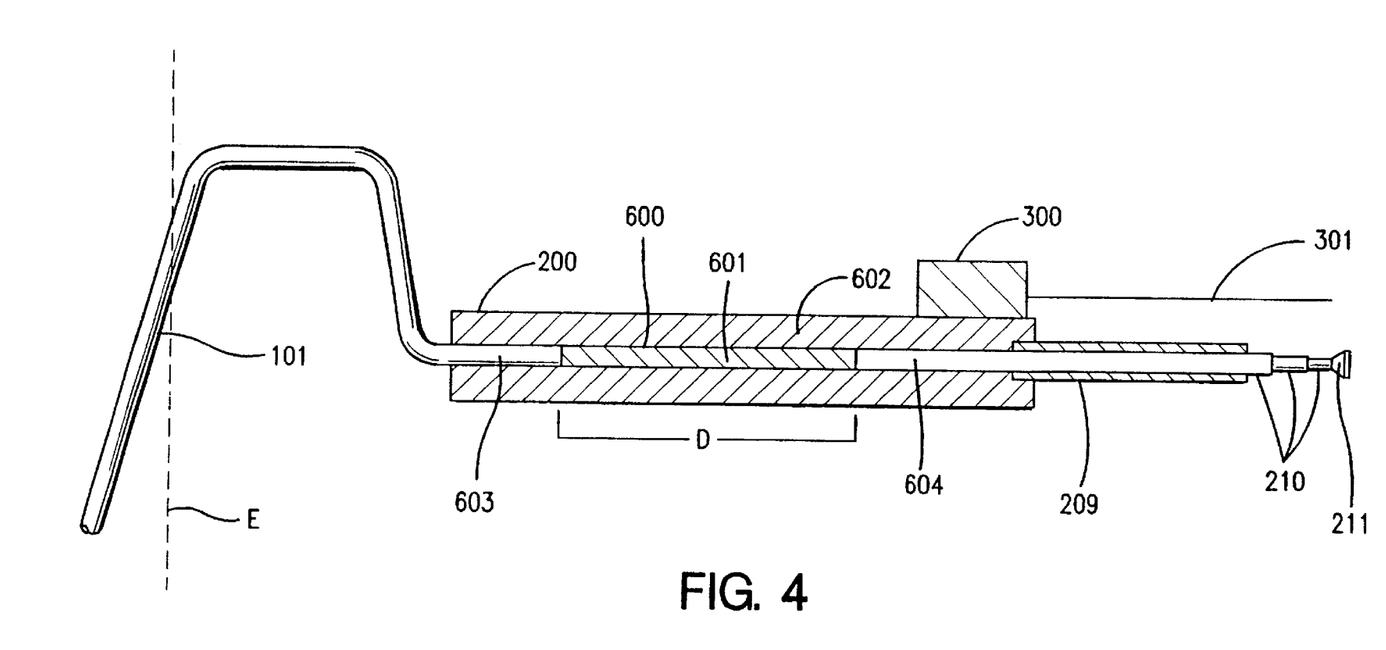
FIG. 4 is a cross sectional view across the length and through the center of the locator device according to the present invention.
Figure 5:
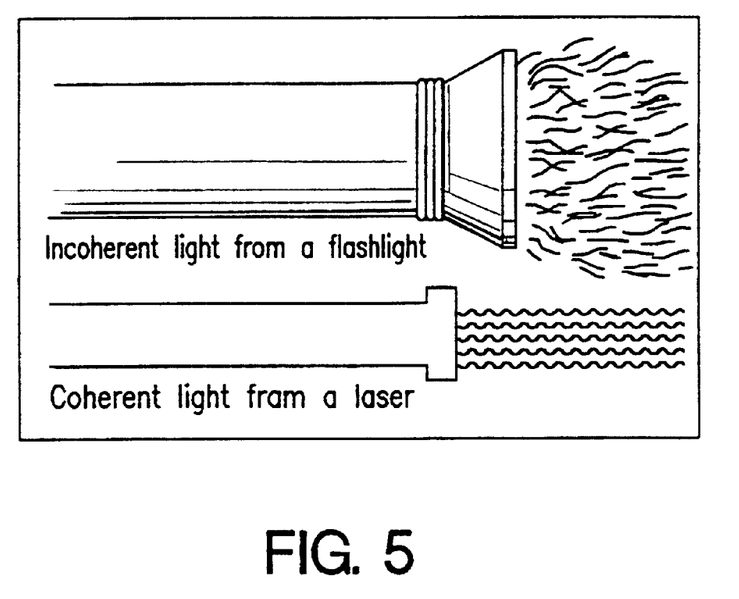
FIG. 5 is a schematic drawing comparing the characteristics of coherent laser beam radiation to characteristics of non-coherent non-laser radiated light.

The interior of the central dielectric housing 200 is shown in FIG. 4, together with the laser 300 and laser beam 301 emanating therefrom. One end 604 of the telescoping antenna 210 extends into the front end of the housing 200, while an end 603 of the handle 101 extends into the rear end of the housing 200. The laser 300 is disposed on the housing. A cavity 600 is filled with a first dielectric material 601 that surrounds both the interior end 604 of the telescoping antenna 210 as well as the interior end 603 of the handle 101. Around this cavity 600 is a second dielectric material 602 that defines the shape of the cavity 600 and also contacts the interior end 604 of the telescoping antenna 210 as well as the interior end 603 of the handle 101 near the point where end 604 and end 603 exit the housing 200. The device's handle 101 with the operator's hand defines a pivot line E around which the dielectrophoretic force produces the subsequent resulting torque, acceleration, vibration or any other measurable, quantifiable manifestation of the force. The ends 604 and 603 are separated by a distance D, which distance is human-operator-specific and also affects the overall sensitivity and response of the locator device 100 with respect to maximum detectable force and torque.

While the specific dielectric materials for maximizing the torque effect on the antenna for different entities are still being researched, dielectrics have been found that produce a usable torque for precisely locating inanimate entities. In particular, the handle 101 and the antenna 102 preferably contain some metal, material 601 is air, material 602 is PVC, and the rear portion 209 of the antenna is nylon. In addition, the circuitry in modules 201, 202, 203 and bottom module 212 is encapsulated in PVC, while the modules themselves, housing 200, as well as the parabolic antennas 207 and 208, are also made of PVC. When these materials are used, an effective dielectrophoretic force and the subsequent resulting torque are detected by the antenna 102 and the device's other component parts to precisely locate the presence of human beings or other entities or objects. Dielectric material 601 may alternately be selected from the following materials with varying levels of resulting torque: water (distilled, deionized), glycerol, (di)ethylene, triethylene glycol, 2-ethyl-1,3-hexanediol, γ-butyrolactone, dimethylpropionamide, di-methyl sulfoxide, methanol, ethanol, 2-propanol, 2-propyl-2 methanol, PVC, ABS, etc., or any one of several well-known engineering plastics, barium titanate, lead titanate, and lead zirconate titanate. Device housing material 602 can be made from polyvinyl chloride, polyurethane, or any one or more of well-known engineering plastics.

Figure 7:
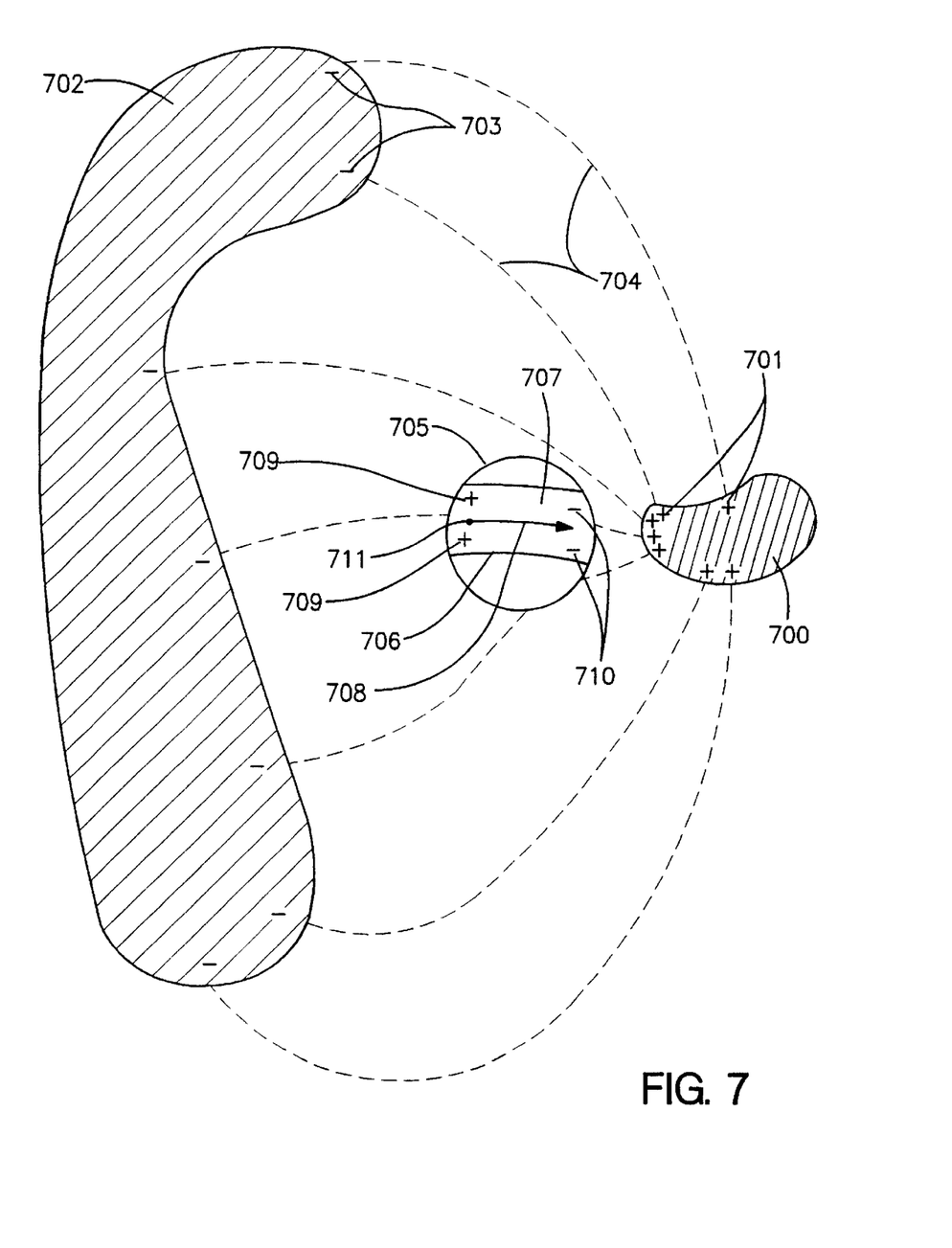
FIG. 7 is a schematic drawing of the dielecrophoresis effect.

FIG. 7 shows a target entity of interest 700 and a surrounding ground plane 702. The entity's polarization charges 701 produce non-uniform electric field lines 704 that have a unique spatial pattern as shown. The non-uniform electric field lines 704 also have a unique spatial gradient pattern (not shown). The non-uniform electric field lines 704 terminate on the surrounding ground plane 702 and induce opposite polarization charges 703 thereon. An initially neutral matter or medium 705, such as the device of the present invention, is shown amidst the non-uniform electric field lines. The neutral matter 705 includes a cavity 706 filled with a specific dielectric material 707. The non-uniform electric field lines induce polarization charges 709 and 710 in the dielectric material 707. The neutral matter 705 also contains protuberant antennas 708 that are formed from a specific dielectric material and are in direct contact with the cavity 706 and the dielectric material 707. The protuberant antennas 708 form a pivot line 711 that is perpendicular to the plane containing FIG. 4. The dielectrophoretic force manifests itself as an easily detected torque motion of the antenna 708 about the pivot line 711.

Figure 8A:
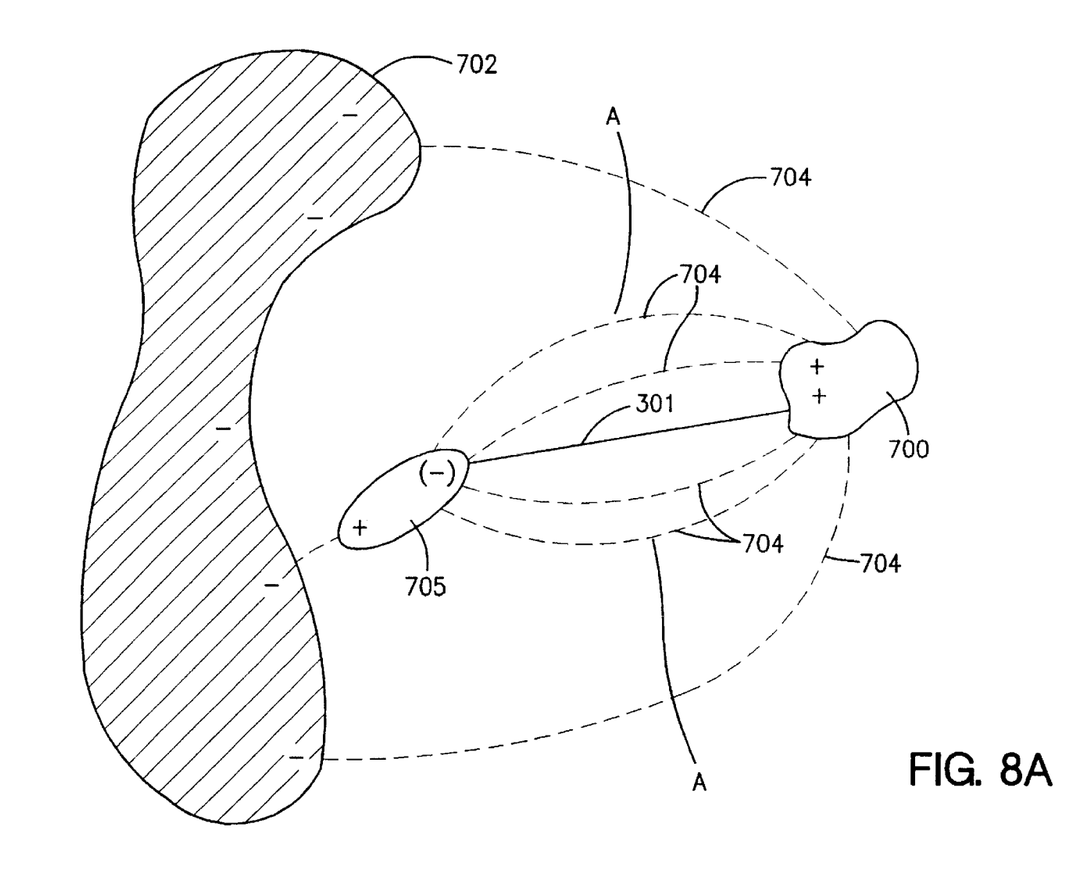
FIG. 8A illustrates the non-uniform electric field lines being oriented toward the higher dielectric constant region where the laser beam occurs.
Figure 8B:
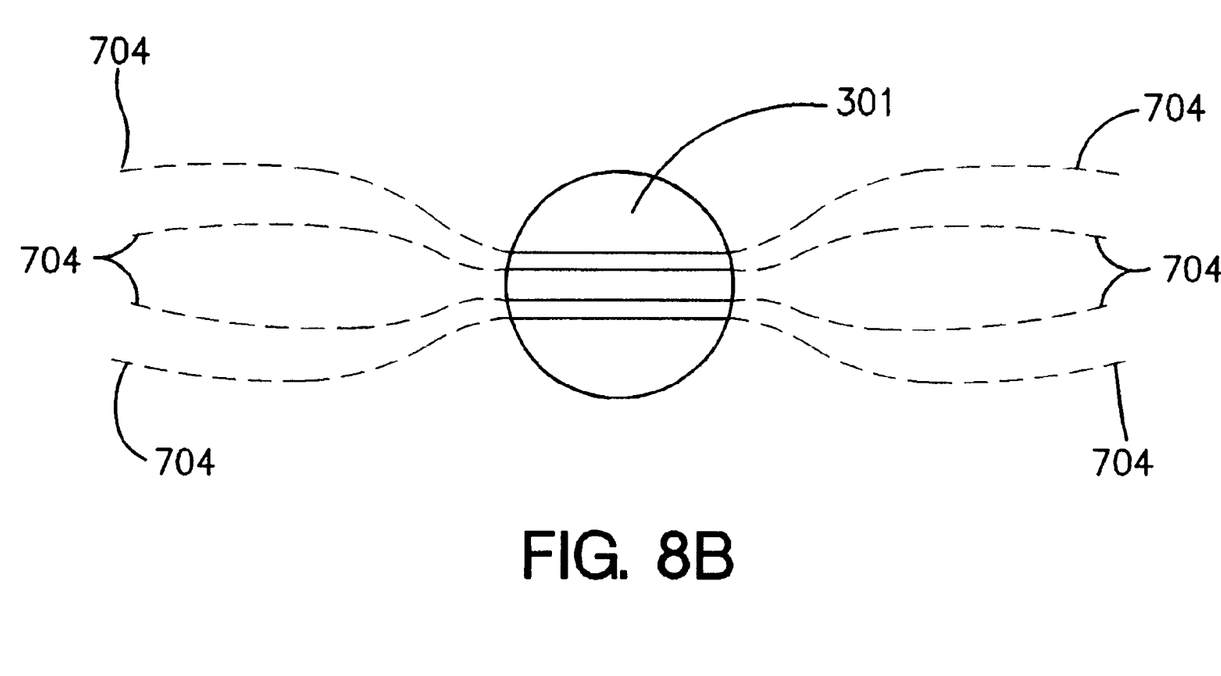
FIG. 8B is a cross section of the non-uniform electric field lines in the vicinity of the laser.

FIG. 8A shows the concentration of electric field lines caused by the introduction of laser radiation via a laser 300 and laser beam 301. When a laser beam 301 is introduced as emanating from the initially neutral body, the non-uniform electric field lines tend to become oriented toward the higher dielectric constant region created by the laser radiation of the laser beam 301. A cross section of the laser beam and electric field lines of FIG. 8A taken across section A—A is shown in FIG. 8B. As shown in FIG. 8B, the non-uniform electric field lines 704 are directionally modified and converged or oriented by the laser beam 301, which, as described herein, creates a region of high dielectric constant.

The inclusion of laser radiation enhances the dielectrokinetic effect by creating a localized region of significantly higher dielectric constant and other properties which in turn significantly increases the dielectrophoretic force and resulting torque, and lowers the response time by preferentially directionally orienting or converging the non-uniformity of the electric field line generated by the entity or target object towards the laser beam region. The laser's effect enhances the operational performance of dielectrokinetic detection devices by improving the range of detection, the strength of force and resulting torque manifestation in the locator device, and the ultimate speed of the locator device. Lasers having total laser radiation power levels in the range of 0.01 milliwatts to 100 megawatts are available, and are helpful in enhancing the dielectrokinetic effect, while power levels in the range of 5 milliwatts to 20 milliwatts are preferred. Lasers having laser radiation wavelengths in the range of $10^8$ nanometers (microwaves) to 10s of nanometers (x-rays) are also available, and serve to enhance the dielectrokinetic effect, while wavelengths in the range of 600 nanometers to 810 nanometers are preferred. It is further noted that these lasers may produce radiation having coherence lengths from the nanometer range to the kilometer range.

As set forth above, and shown in FIG. 9, multiple lasers may be added to a given locator device to further enhance the dielectrokinesis force and torque. The lasers are simultaneously operating while being directly attached to the locator device, where their beams are all parallel to the locator device antenna. For a given number of lasers, the optimal geometrical arrangement for maximum laser enhancement has been found to be the arrangement with the highest symmetry. For example, two lasers should be disposed linearly, three lasers (as shown in the example of FIG. 9) should be arranged at the corners of an equilateral triangle, four lasers should be arranged at the corners of a square, and so on.

While this invention has been described in conjunction with specific embodiments thereof, it is evident that many alternatives, modifications and variations will be apparent to those skilled in the art. Accordingly, the preferred embodiments of the invention, as set forth herein, are intended to be illustrative, not limiting. Various changes may be made without departing from the true spirit and full scope of the invention, as defined in the claims.

What is claimed is:

1. A device for locating either an entity or an object of a predetermined type, comprising:

a housing formed of a first dielectric material and having an interior with a second dielectric material therein;

a source of laser radiation disposed on said housing and directed substantially parallel to a longitudinal axis of the device; and a handle formed of a conductive material disposed in contact with said second dielectric material, said handle being constructed such that the device reacts to produce a dielectrophoretic force and quantifiable manifestation of said force in the device, said force being associated with a non-uniform electric field pattern of said entity or object being detected and being enhanced by incorporation of the laser radiation, said force directionally orienting the device toward said entity or object being detected.

2. The device according to claim 1, wherein said source of laser radiation comprises plural lasers.

3. The device according to claim 2, wherein said plural lasers are arranged in geometrically optimal positions about said housing.

4. The device according to claim 3, wherein said source of laser radiation operates at a wavelength of 600 nanometers.

5. The device according to claim 3, wherein said source of laser radiation operates at a wavelength of 808 nanometers.

6. The device according to claim 3, wherein said source of laser radiation operates at a wavelength of 632.8 nanometers.

7. The device according to claim 1, wherein said source of laser radiation produces a total power output in the range of 0.01 milliwatts to 100 megawatts.

8. The device according to claim 1, wherein said source of laser radiation produces laser radiation having a coherence length in the range from nanometers to kilometers.

9. The device according to claim 1, wherein said source of laser radiation operates at a wavelength in the range of $10^8$ nanometers to 10 nanometers.

10. The device according to claim 9, wherein said source of laser radiation operates at a wavelength of 600 nanometers.

11. The device according to claim 10, wherein said source of laser radiation produces radiation power of 5 milliwatts.

12. The device according to claim 10, wherein said source of laser radiation produces radiation power of 20 milliwatts.

13. The device according to claim 10, wherein said source of laser radiation produces laser radiation with a coherence length in the millimeter range.

14. The device according to claim 9, wherein said source of laser radiation operates at a wavelength of 808 nanometers.

15. The device according to claim 14, wherein said source of laser radiation produces radiation power of 5 milliwatts.

16. The device according to claim 14, wherein said source of laser radiation produces radiation power of 20 milliwatts.

17. The device according to claim 14, wherein said source of laser radiation produces laser radiation with a coherence length in the millimeter range.

18. The device according to claim 9, wherein said source of laser radiation operates at a wavelength of 632.8 nanometers.

19. The device according to claim 18, wherein said source of laser radiation produces radiation power of 5 milliwatts.

20. The device according to claim 18, wherein said source of laser radiation produces radiation power of 20 milliwatts.

21. The device according to claim 18, wherein said source of laser radiation produces laser radiation with a coherence length in the range of tens of centimeters.

22. A method of locating either an entity or an object of a predetermined type, said method comprising the steps of:

providing a locating device having a housing which is formed of a first dielectric material and having an interior with a second dielectric material therein, providing a source of laser radiation directed substantially parallel to a longitudinal axis of the device, and a handle;

holding the locating device by said handle which is formed of a conductive material disposed in contact with said second dielectric material, said handle being constructed such that the device reacts to produce a dielectrophoretic force and quantifiable manifestation of said force in the device;

scanning said locating device in a general direction of said entity or object to be detected while the laser source emits laser radiation; and observing a directional orientation of said device caused by a detectable manifestation of a dielectrophoretic force produced by an interaction between said device and said entity or object and enhanced by incorporation of the laser radiation.

23. The method according to claim 22, wherein the entity being detected is an animate entity.

24. The method according to claim 23, wherein the animate entity is selected to be at least one entity from the group comprising: human beings, mammals, birds, reptiles, amphibians, fishes, protozoa, parazoa and metazoa.

25. The method according to claim 22, wherein the object being detected is an inanimate object.

26. The method according to claim 25, wherein the inanimate object is selected to be at least one object from the group comprising: plastic material comprising one or more pure polymers, non-plastic organic material, inorganic material, a metallic conductor, water, and an actinide element with an atomic number greater than 89.

27. The method according to claim 26, wherein said group of metallic conductors includes gold, silver, platinum or palladium.

28. The method according to claim 25, wherein the inanimate object is a plant.

29. The method according to claim 25, wherein the inanimate object is an explosive material.

30. The method according to claim 25, wherein the inanimate object comprises at least one of various chemical compounds known to alter normal cardiac and neural biochemistry of human beings.

31. A locating device for locating either an entity or an object of a predetermined type comprising a polarization unit, including a source of laser radiation directed substantially parallel to a longitudinal axis of the device, that detects a polarization charge pattern in accordance with a spatially non-uniform electric field exhibited by a target entity while said source of laser radiation emits radiation in a direction toward the target entity, the locating device reacting to the polarization charge pattern to produce a dielectrophoretic force and quantifiable manifestation of said force in the device, said force being enhanced by incorporation of the laser radiation, said force directionally orienting the device toward said entity or object being detected.

32. The locating device according to claim 31, wherein said source of laser radiation comprises a plurality of lasers.

33. A method for locating a target entity with a locating device, the method comprising:

emitting laser radiation from the locating device in a direction substantially parallel to a longitudinal axis of the device; and detecting a polarization charge pattern in accordance with a spatially non-uniform electric field exhibited by the target entity by reacting to the polarization charge pattern to produce a dielectrophoretic force and quantifiable manifestation of said force in the device, the force being enhanced by incorporation of the laser radiation, said force directionally orienting the device toward said entity or object being detected.

* * * * *